United States Patent [19]

Meister

[11] Patent Number: 4,784,685

[45] Date of Patent: Nov. 15, 1988

[54] GLUTATHIONE DELIVERY SYSTEM

[75] Inventor: Alton Meister, New York, N.Y.

[73] Assignee: Cornell Research Foundation, Inc., Ithaca, N.Y.

[21] Appl. No.: 68,306

[22] Filed: Jul. 1, 1987

Related U.S. Application Data

[60] Division of Ser. No. 817,696, Jan. 10, 1986, which is a continuation-in-part of Ser. No. 557,555, Dec. 2, 1983, abandoned.

[30] Foreign Application Priority Data

Apr. 22, 1985 [JP] Japan .................................. 60-86974
Apr. 22, 1985 [JP] Japan .................................. 60-86975

[51] Int. Cl.⁴ .............................................. A01N 37/00
[52] U.S. Cl. .................................................... 71/106
[58] Field of Search ......................................... 71/106

[56] References Cited

FOREIGN PATENT DOCUMENTS 2016668 8/1968 Japan.
108399 7/1985 Japan.

OTHER PUBLICATIONS

Proc. Nat'l. Acad. Sci. U.S.A.; vol. 80, pp. 5258–5260 (1983).
Archives of Biochem. and Biophys., vol. 239, No. 2, pp. 538–548 (1985).
Wellner, et al.; Prox. Natl., Acad. Sci. U.S.A.; vol. 81, pp. 4732–4735, Aug. 1984.

*Primary Examiner*—Delbert R. Phillips
*Attorney, Agent, or Firm*—Sughrue, Mion, Zinn, Macpeak & Seas

[57] ABSTRACT

Substantially pure alkyl monoesters of glutathione, the ester being of the glycine carboxylic acid, and use thereof to increase cellular levels of glutathione.

14 Claims, 3 Drawing Sheets

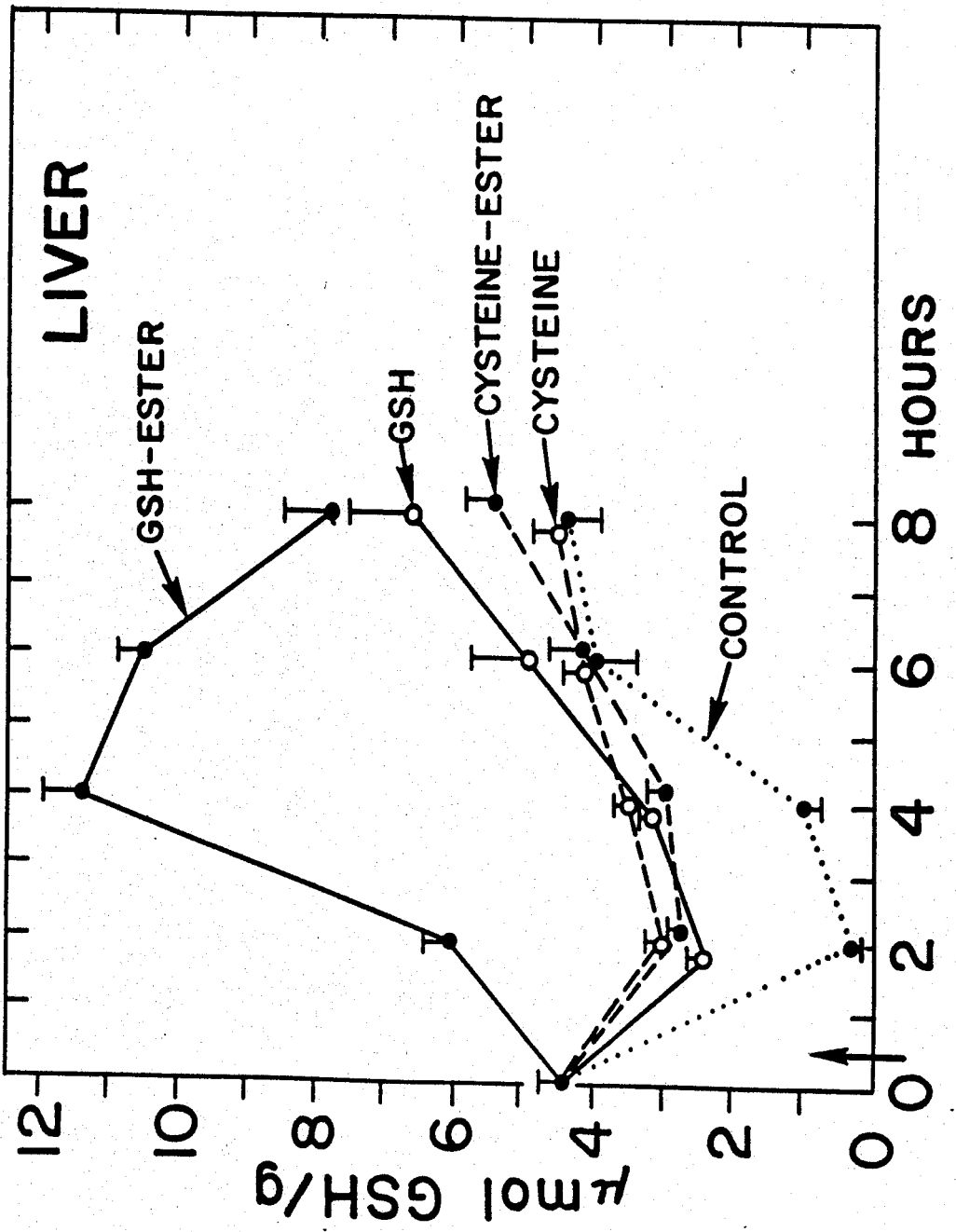

GLUTATHIONE DELIVERY SYSTEM

BACKGROUND OF THE INVENTION

The present invention relates to a method for increasing cellular levels of glutathione. This invention was made with government support under contract DAM17-83-C-3020 awarded by the United States Army. The Government has certain rights in this invention.

This is a division of application Ser. No. 817,696, filed Jan. 10, 1986, which is a continuation-in-part of application Ser. No. 557,555, filed Dec. 2, 1983, now abandoned.

DESCRIPTION OF THE PRIOR ART

It is well-known that the tripeptide thiol glutathione (L-$\gamma$-glutamyl-L-cysteinyl-glycine; GSH) found in virtually all cells functions in metabolism, transport and cellular protection. Glutathione functions in the reduction of the disulfide linkages of proteins and other molecules, in the synthesis of the deoxyribonucleotide precursors of DNA, and in the protection of cells against the effects of free radicals and of reactive oxygen intermediates such as peroxides that are formed in metabolism.

Modifications of glutathione metabolism may be achieved by administration of selective enzyme inhibitors to decrease intracellular glutathione levels, or by providing compounds that increase glutathione synthesis. Such effects are useful in chemotherapy and radiation therapy and in protecting cells against the toxic effects of drugs, other foreign compounds and oxygen. Indeed, the diverse functions of GSH are relevant to many fields of biology, including not only enzymology and transport but also pharmacology, radiation biology, cancer therapy, toxicology, endocrinology, microbiology and agriculture. The enzymatic and transport phenomena of glutathione metabolism are outlined in Meister. "Selective Modification of Glutathione Metabolism", *Science*, Volume 220, Number 4596, 472–477 (April 1983), which is hereby incorporated by reference.

Modification of GSH metabolism to deplete or increase cellular GSH may serve various purposes. For instance, it has long been known that thiols protect cells against the effects of irradiation. Since decreasing cellular GSH makes cells more susceptible to irradiation, glutathione depletion is useful in chemotherapeutic situations in which the cells to be killed and the cells to be spared have substantially different quantitative requirements for GSH. Depletion of GSH by inhibition of its synthesis also serves as a valuable adjuvant in chemotherapy with drugs that are detoxified by reactions involving GSH.

Conversely, development of resistance to a drug or to radiation may be associated with an increase in cellular GSH. GSH serves effectively in the detoxification of many drugs, and it is known that a significant pathway of acetaminophen detoxification involves conjugation with GSH.

Treatment with a thiazolidine such as L-2-oxothiazolidine-4-carboxylic acid, may be of value to patients with liver disease and to premature infants who may be deficient in the utilization of methionine sulfur for cysteine formation, and thus in GSH synthesis. The effectiveness of such a thiazolidine as an intracellular cysteine precursor depends on the presence of 5-oxoprolinase, an enzyme activity found in almost all animal cells. This enzyme also occurs in plants, suggesting that such a thiazolidine, and hence glutathione, may be useful as a safener in agriculture to protect crop plants against the toxic effects of herbicides.

Various methods are known to increase cellular levels of glutathione. Glutathione is composed of three amino acids: glutamic acid, cysteine and glycine. Administration to animals of the amino acid precursors of glutathione may produce an increase in cellular glutathione, but there is a limit to the effectiveness of this procedure. Concentrations of GSH are dependent on the supply of cysteine, which is derived from dietary protein and by trans-sulfuration from methionine in the liver. Administration of cysteine is not an ideal way to increase GSH concentration because cysteine is rapidly metabolized and furthermore, it is very toxic. Administration to animals of compounds that are transported into cells and converted intracellularly into cysteine is sometimes useful in increasing cellular glutathione levels. For example, the thiazolidine L-2-oxothiazolidine-4-carboxylate is transported into the cell, where it is converted by 5-oxoprolinase to L-cysteine, which is rapidly used for GSH synthesis.

Another way in which tissue GSH concentration may be increased is by administration of $\gamma$-glutamylcysteine or of $\gamma$-glutamylcystine. The administered $\gamma$-glutamyl amino acid is transported intact and serves as a substrate of GSH synthetase. It is also known that administration of N-Acetyl-L-cysteine increases tissue concentrations of GSH.

That the administration of glutathione itself might lead to increased glutathione levels has also been considered. However, there is no published evidence that shows that intact glutathione enters cells. In fact, there are several reports on particular biological systems indicating that glutathione itself is not transported into cells. The increase in cellular glutathione sometimes found after administration of glutathione is due to (a) extracellular breakdown of glutathione, (b) transport into cells of free amino acids or dipeptides derived from glutathione extracellularly, and (c) intracellular resynthesis of glutathione.

These previous methods of increasing intracellular glutathione concentration are disadvantageous in the areas of efficiency, toxicity, limits on effective concentration obtainable, etc. as discussed heretofore. In addition, the known methods which depend on synthesis of GSH by increasing the supply of substrates to the two synthetases involved, depend on the presence of the synthetases, the first of which is subject to feedback inhibition by GSH.

Accordingly, an object of the invention is to provide a method for increasing the intracellular levels of glutathione by delivering intact glutathione to the cell rather than its amino acid substrates.

A further object of the invention is to provide pure derivatives of glutathione, the use thereof in glutathione delivery and a method for obtaining such pure derivatives.

Another object of the invention is to provide a method of increasing intracellular levels of glutathione which is highly efficient and which does not depend on the presence of synthetases.

A further object of the present invention is to provide a method for increasing the intracellular levels of glutathione without the toxic effects of other known methods.

Still another object of the invention is to provide a method for efficiency and rapidly increasing cellular glutathione levels for any purpose for which elevated glutathione levels are desired in the prior art, such as for drug detoxification, cellular protection against oxygen and its metabolites such as peroxides, free radicals, or foreign compounds, etc.

SUMMARY OF THE INVENTION

The present invention overcomes the difficulties of toxicity, limited effectiveness, and dependence on cellular synthetases encountered in previously known methods of increasing intracellular glutathione concentration. More specifically, the above and other objects have been attained by a method for increasing intracellular glutathione levels by administering an alkyl monoester of glutathione, with the esterification occurring at the glycine carboxylic acid group. Such esters are transported into, for example, liver and kidney cells, and are de-esterified within the cells, thus leading to increased cellular levels of glutathione. The alkyl group can contain 1 to 10 carbon atoms, preferably 1 to 3 carbon atoms.

By the present method involving administration of GSH esters, increased levels of GSH are provided in an efficient, rapid manner.

In addition, the present invention provides the pure alkyl esters, and a method to produce them as disclosed hereinafter.

BRIEF DESCRIPTION OF THE DRAWINGS

FIG. 3 is a graph plotting the glutathione levels of the livers of mice previously given acetaminophen.

DESCRIPTION OF PREFERRED EMBODIMENTS

Figure 1A:
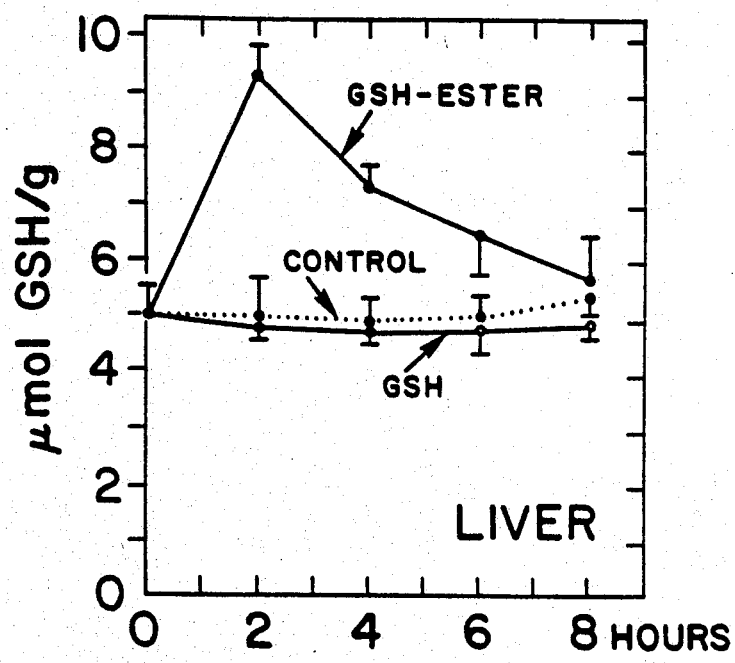
FIGS. 1(a) and 1(b) are graphs plotting the glutathione levels of the liver and kidney of fasted mice given glutathione ester and glutathione itself in comparison with controls.

By the present method, esterified glutathione is transported intact into the cell, where it is de-esterified by the action of hydrolase, thus leading to increased cellular levels of glutathione. Glutathione has two carboxyl groups, one on the glutamic acid residue and one on the glycine residue. The compounds used in the present method are alkyl esters of glutathione in which only the glycine carboxyl group is esterified. Thus, the compounds used in the present invention have the structure:

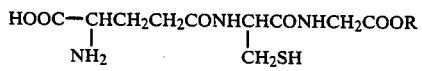

wherein R is an alkyl group containing 1 to 10 carbon atoms. Pharmaceutically acceptable salts of the above compounds are within the scope of the present invention.

The alkyl group of the GSH monoalkyl ester according to the invention is a saturated, straight or branched, alkyl group of 1 to 10 carbon atoms and includes preferably a saturated straight alkyl group such as methyl, ethyl, propyl, butyl, pentyl, hexyl, heptyl, octyl, nonyl or decyl and a saturated branched alkyl group such as isopropyl, isobutyl, sec-butyl, tert-butyl or isopentyl. Among them, methyl, ethyl, isopropyl and isobutyl are especially suitable for medical use, because their intracellular GSH level elevating activity is excellent and they are easily obtainable in the crystalline form.

The source of glutathione used in the present invention is not important, and thus glutathione may be synthesized or isolated by methods conventional in the art or purchased.

The esterification procedure used can be selected from those conventional in the art, as long as the esters are subjected to sufficient purification so that on a weight basis, the monoester is at least 98% pure, preferably at least 99% pure. The reason for this is that conventional processes described in prior art such as treatment with ethanolic HCl, yield monoester having diester admixed therewith, for example at a level of about 5 to 20% by weight. The dimethylester has been found to be toxic to mice. An overall process to yield pure monoester is set forth in Synthesis examples hereinafter. The monoester is very water soluble at a basic pH while the diester is organic solvent soluble at basic pH. Thus, the impure product obtained by a conventional synthesis is dissolved in water, pH is adjusted to about 8.0 to 9.2 using a convenient base such as an amine and then extraction is carried out using an organic solvent immiscible with water, such as chloroform, ethyl acetate, and the like.

The GSH monoalkyl ester can be chemically prepared by reacting GSH with an alcohol (ROH in which R is an alkyl group of 1 to 10 carbon atoms) containing hydrogen chloride at room temperature or under cooling (for example, 0° to 25° C.) over a period of from several hours to several days to give the hydrochloride of the GSH monoalkyl ester.

In this case, the esterification proceeds predominantly on the carboxyl group of the glycine moiety but hardly on the carboxyl group of the glutamic acid moiety. Even if the esterification proceeded on both sides to a certain extent, the monoester can be easily separated from the diester utilizing the difference of the solubility between them; as noted above the monoester is, in general, easily soluble in water at a basic pH range while the diester is easily soluble in organic solvents.

Further, the GSH monoalkyl ester hydrochloride can be effectively converted into its free monoalkyl ester by treating with an ion exchange resin such as HP-20 column or the like. If necessary, purification with activated carbon may be applied thereto.

Further, the GSH monoalkyl ester can be separated from impurities of glutathione diester and glutathione by chromatography on weak cation exchange columns such as IRC-50.

As the alcohol, there may be used the one corresponding to the objective ester, and preferred are a straight saturated alcohol such as methyl alcohol, ethyl alcohol, propyl alcohol, butyl alcohol, pentyl alcohol, hexyl alcohol, heptyl alcohol, octyl alcohol, nonyl alcohol or decyl alcohol and a branched saturated alcohol such as isopropyl alcohol, isobutyl alcohol, sec-butyl alcohol, tert-butyl alcohol, isopentyl alcohol or neopentyl alcohol.

It is advantageous that the reaction of GSH with the alcohol in the presence of hydrochloric acid as described above facilitates isolation of the ester hydrochloride produced, which can be neutralized by a simple operation into its free ester.

The esters of glutathione are typically administered by injection after dissolution in water. However, the esters are also effective after oral administration. The esters can be admixed with suitable pharmaceutically acceptable carriers such as the aforementioned water or physiological saline solution in the preparation of liquid formulations or with lactose, sucrose, starch, talc or the like in formulating powders.

A suitable therapeutically effective dosage can be selected based on routine experimentation, particularly in view of prior art uses for glutathione and the examples hereinafter, bearing in mind the approximately stoichiometric intracellular, hydrolysis believed to occur. In any event, one can monitor glutathione level in the patient or use other parameters of effectiveness depending on the nature of the toxicity being treated. At this time, a suggested dosage is about 0.5 to 10 millimoles of ester per kg of body weight, preferably about 2 to 5 millimoles of ester per kg of body weight, one to six times a day.

Administration is carried out to typically result in intracellular levels of glutathione of 0.5 to 3 millimoles within 0.5 to 2 hours after administration.

Although the precise mechanism of the reaction is not known, the increase in intracellular glutathione obtained by the present method is interpreted to indicate that the administered glutathione ester is transported into the cells of at least the liver and kidney where it is hydrolyzed to glutathione. Such hydrolysis has been demonstrated in in vitro experiments in which glutathione monoesters were incubated with homogenates of liver and kidney.

Having thus described in broader terms embodiments of the present invention, the following more detailed description is provided with reference to specific examples.

SYNTHESIS EXAMPLE 1

Preparation of the Monoethyl Ester of Glutathione (L-γ-Glutamyl-L Cysteinyl Glycyl Ethyl Ester)

Glutathione (20 grams) was treated with 100 ml of ethanol containing 4.8 grams of hydrogen chloride in a glass-stoppered vessel, which was placed at 0° C. for 6 hours. After addition of 200 ml of cold ethanol, triethylamine was added to bring the pH to 6. The mixture was allowed to stand for 18 hours at 0° C. and the precipitate which formed was collected by filtration. The precipitate was dissolved in 100 ml of water and cooled to 0° C. The pH of this solution was adjusted to 8.8 by addition of triethylamine and the solution was rapidly extracted 3 times with 250 ml portions of chloroform. The aqueous layer was rapidly adjusted to pH 5 by addition of 6M hydrochloric acid and the solvent was removed by flash evaporation under reduced pressure. The dried product was triturated with dry diethyl ether and ethanol. The crystals obtained were filtered and washed with diethyl ether. The product was dried under vacuum over phosphorous pentoxide and calcium chloride. The product was re-crystallized from aqueous ethanol. The yield was 80–90%.

SYNTHESIS EXAMPLE 2

Isopropyl γ-L-glutamyl-L-cysteinylglycinate (GSH monoisopropyl ester)

(i) To a dispersion of 50.0 g of GSH in 200 ml of isopropyl alcohol, 50 ml of an isopropyl alcohol solution containing 12.0 g of hydrogen chloride were added under stirring and ice cooling. Stirring was continued under ice cooling over a period of about 2 hours. The reaction mixture was then allowed to stand at room temperature over a period of 2 days for esterification. After removal of the isopropyl alcohol from the reaction mixture by evaporation under reduced pressure, the residue was admixed with 400 ml of ether. The powdery product was collected by filtration and washed with ether to give 54.5 g of GSH monoisopropyl ester hydrochloride.

(ii) A solution of 50.0 g of the GSH monoisopropyl ester hydrochloride as above prepared in 70 ml of water was charged on 1.5 liters of HP-20 (ion exchange resin), which was eluted with methanol/water (=20/80 to 40/60). The eluates were combined together and concentrated to give 15.0 g of GSH monoisopropyl ester as crystals. The filtrate was combined with the washings and lyophilized to give 10.5 g of GSH monoisopropyl ester. The total amount of GSH monoisopropyl ester as obtained was 25.5 g.

Physical data

M.P., 184°–186° C.;

IR (KBr, cm$^{-1}$): 1730, 1635, 1525, 1400, 1370, 1205, 1100; $[\alpha]_D^{21}$: −31.0° (c=1.0, H$_2$O);

NMR (DMSO-d$_6$, δ) 1.20 (6H, d, J=6 Hz); 1.72–2.16 (2H, m); 2.20–2.40 (2H, m); 2.64–2.86 (2H, m); 3.20–3.56 (1H, m); 3.80 (2H, s); 4.20–4.60 (1H, m); 4.68–5.08 (1H, m).

SYNTHESIS EXAMPLE 3

Isobutyl γ-L-glutamyl-L-cysteinylglycinate (GSH monoisobutyl ester)

(i) To a dispersion of 20.0 g of GSH in 100 ml of isobutyl alcohol, 16 ml of an isobutyl alcohol solution containing 4.8 g of hydrogen chloride were added at room temperature under stirring. The resultant mixture was stirred at room temperature over a period of 24 hours for esterification. Isobutyl alcohol was evaporated from the reaction mixture under reduced pressure. The residue was admixed with 200 ml of ether. The powdery product was collected by filtration and washed with ether to give 27.0 g of GSH monoisobutyl ester hydrochloride.

(ii) A solution of 12.0 g of the GSH monoisobutyl ester hydrochloride as prepared above in 20 ml of water was charged on 0.5 liter of HP-20 (ion exchange resin), which was eluted with methanol/water (=20/80 to 60/40). The eluates were combined together and concentrated to give 1.9 g of GSH monoisobutyl ester as crystals. The filtrate was combined together with the washings and lyophilized to give 5.2 g of GSH monoisobutyl ester. The total amount of CSH monoisobutyl ester as obtained was 7.1 g.

Physical data

M.P., 186°–190° C.;

IR (KBr, cm$^{-1}$): 1740, 1635, 1530, 1400, 1200, 1095; $[\alpha]_D^{26}$: −24.5° (c=1.0, H$_2$O);

NMR (DMSO-d$_6$, δ): 0.88 (6H, d, J=6 Hz); 1.60–2.12 (3H, m); 2.12–2.44 (2H, m); 2.60–3.00 (2H, m); 3.16–3.44 (1H, m); 3.60–4.04 (3H, m); 4.20–4.60 (1H, m).

SYNTHESIS EXAMPLE 4 n-Hexyl γ-L-glutamyl-L-cysteinylglycinate (GSH mono-n-hexyl ester)

(i) To a dispersion of 10.0 g of GSH in 100 ml of n-hexyl alcohol, 10 ml of an n-hexyl alcohol solution containing 2.4 g of hydrogen chloride were added at room temperature under stirring, and the resultant mixture was stirred at room temperature over a period of 24 hours for esterification. n-Hexyl alcohol was evaporated from the reaction mixture under reduced pressure to give 18.0 g of GSH mono-n-hexyl ester hydrochloride.

(ii) A solution of 9.0 g of the GSH mono-n-hexyl ester hydrochloride as prepared above in 100 ml of water was charged on 0.5 liter of HP-20 (ion exchange resin), which was eluted with methanol/water (=60/40 to 80/20). The eluates were combined together and concentrated to dryness, whereby 2.6 g of GSH mono-n-hexyl ester was obtained as a waxy substance.

Physical data

IR (KBr, cm$^{-1}$): 1740, 1635, 1520, 1400, 1340, 1300, 1200, 1090; $[\alpha]_D^{26}$: −25.2° (C=1.0, CH$_3$OH);

NMR (DMSO-d$_6$, δ): 0.60–1.04 (3H, m); 1.04–1.76 (8H, m); 1.76–2.16 (H, m); 2.16–2.48 (2H, m); 2.60–3.04 (2H, m); 3.20–3.56 (1H, m); 3.82 (2H, s); 3.92–4.20 (2H, m); 4.20–4.60 (1H, m).

SYNTHESIS EXAMPLE 5

Isopropyl γ-L-glutamyl-L-cysteinylglycinate (GSH monoisopropyl ester)

To a solution of 3.85 g of GSH monoisopropyl ester hydrochloride as obtained in Synthesis Example 2 (i) in 10 ml of water, 10 ml of 9.5% aqueous sulfuric acid solution and 0.72 g of cuprous oxide (Cu$_2$O) were added in order, and the resultant mixture was warmed on a water bath at a temperature of 50° C. over a period of 5 minutes, stirred at room temperature over a period of 2 hours and allowed to stand in an ice box overnight. The precipitated copper salt of GSH monoisopropyl ester was transferred on a ratiolarite and washed with suction until the washing became neutral.

Said wet precipitate inclusive of the ratiolarite was taken out and dispersed in 50 ml of water. Hydrogen sulfide gas was introduced into the dispersion over a period of 1 hour, followed by filtration. Into the filtrate, nitrogen was introduced, whereby the hydrogen sulfide was expelled therefrom. The filtrate was lyophilized to give 1.26 g of GSH monoisopropyl ester.

Physical data of GSH monoisopropyl ester thus obtained were identical to those of the authentic sample obtained in Synthesis Example 2.

SYNTHESIS EXAMPLE 6 n-Propyl γ-L-glutamyl-L-cysteinylglycinate (GSH mono-n-propyl ester)

The reaction was performed in the same manner as in Synthesis Example 2 except that n-propyl alcohol was used in place of isopropyl alcohol, whereby GSH mono-n-propyl ester hydrochloride was obtained.

The product was subjected to thin layer chromatography (25° C., 10–20 minutes) using silica gel (MK6F; Analtech; 1×3 inches, 200µ thick) and n-propyl alcohol/acetic acid/water (=10:1:5 by volume) as a developing solution to give an Rf value of 0.68 (colored in pink by spraying 0.5% ninhydrin-acetone solution).

Eluting period was 58.5 minutes according to the amino acid analyzer (Durrum model 500) using lithium buffer.

EXAMPLE 1

The glutathione monomethyl ester was used (99% purity). A solution of the glutathione ester was prepared in aseptic water. Mice weighing 20 to 50 grams, obtained from Taconic Farms, Incorporated, (TAC: (SWFBR)), were fasted for 24 hours and intraperitoneally injected with the glutathione monomethyl ester in a dose of 10 millimoles per kilogram. At intervals of 2 hours, as shown in FIGS. 1(a) and (b), the animals were decapitated and the liver and kidney tissues were removed and analyzed for glutathione. Using groups of 3 mice each, values are given as means ±S.D.

As shown in FIGS. 1(a) and (b), the glutathione level of the liver of animals treated with glutathione ester increased substantially 2 hours after administration. The levels then declined gradually. Also, the value of glutathione in the kidney increased substantially after 2 hours and then declined. Controls were given an equivalent volume of 0.15M sodium chloride, and showed no increase in either liver or kidney glutathione levels.

EXAMPLE 2

Figure 2A:
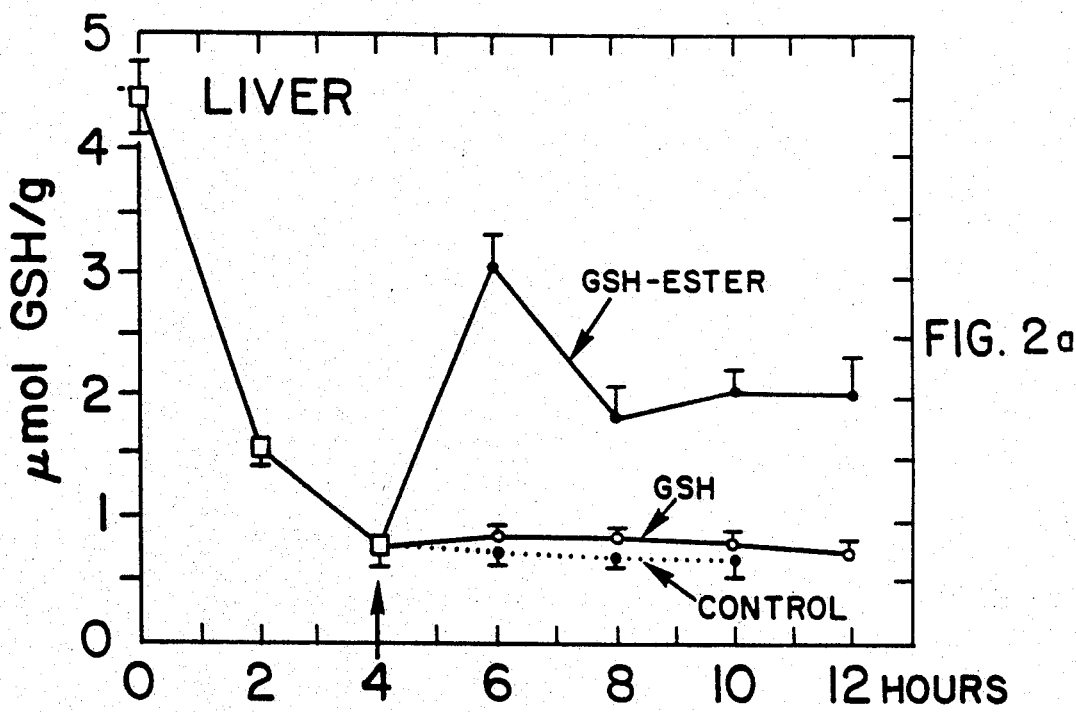
FIGS. 2(a) and 2(b) are graphs plotting the glutathione levels of mice pretreated with buthionine sulfoximine.
Figure 2B:
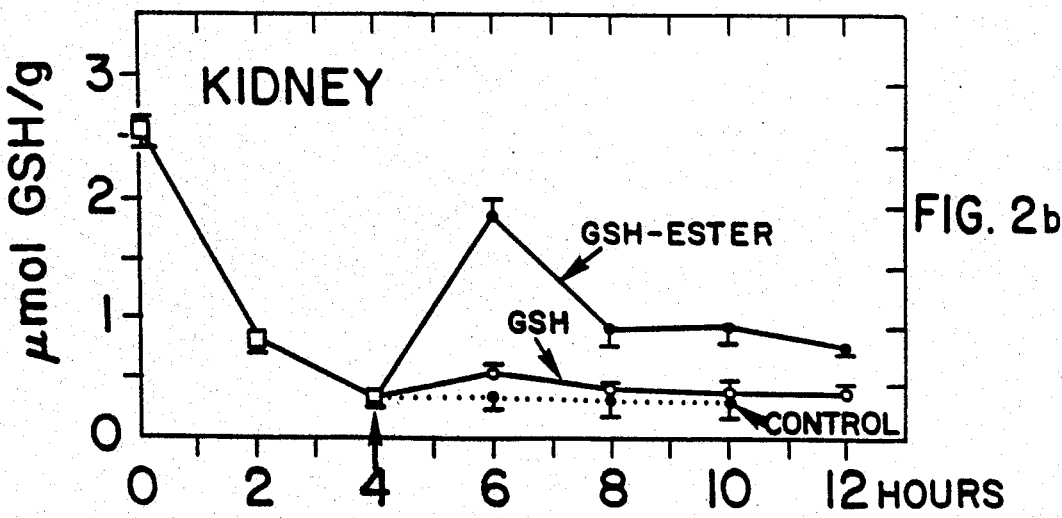

Mice were administered the methyl ester of glutathione as in Example 1, with the only difference being that the animals were pretreated with 2 mmol/kg buthionine sulfoximine, an effective inhibitor of glutathione synthesis, with the GSH-ester being administered 4 hours after the inhibitor. In this experiment, the glutathione levels of the liver and kidney initially decreased to a very low value because the enzyme (γ-glutamylcysteine synthetase) required for glutathione synthesis was markedly inhibited by buthionine sulfoximine. When methyl esters of glutathione were administered to the pre-treated animals, there was a substantial increase in the glutathione levels in both liver and kidney. See FIGS. 2(a) and (b). Controls were again given saline, with tissue levels of GSH being determined at the indicated intervals. Values are means ±S.D., using groups of 3 mice each.

COMPARATIVE EXAMPLE 1

Figure 1B:
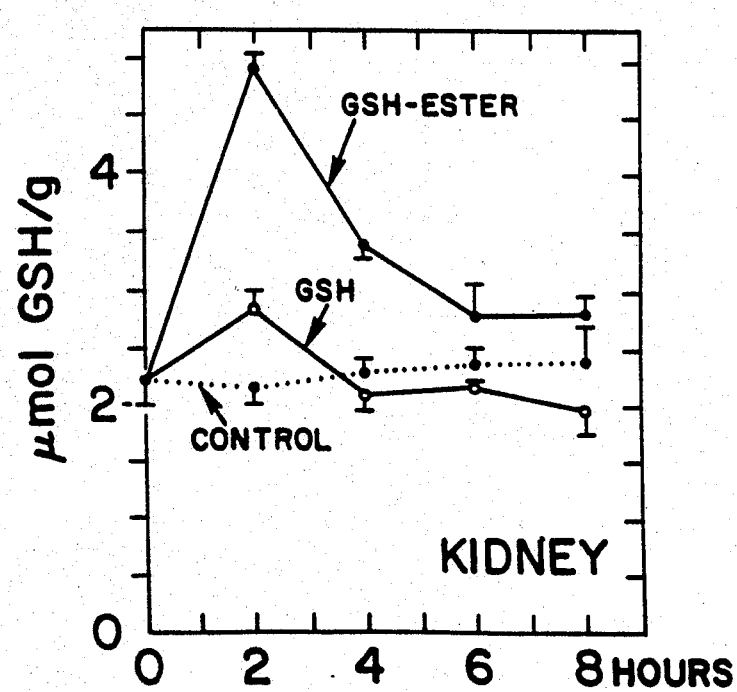

Example 1 was repeated with the substitution of glutathione for glutathione monomethyl ester, in the same dosage. As shown in FIGS. 1(a) and 1(b), no effect was seen in the glutathione level of the liver of the controls and only a slight effect is noted with glutathione itself in the kidney, as compared to the controls in which there was essentially no change.

The effects observed with glutathione monomethyl ester are above the same as found with glutathione monoethyl ester.

EXAMPLE 3

Mice treated with a sublethal dose of acetaminophen showed a marked decrease in the level of liver glutathione (FIG. 3; control). No such decline in glutathione levels was found in mice treated with acetaminophen followed by injection of glutathione monomethyl ester. In contrast the glutathione level of the liver increased markedly. Under the same conditions, administration of the other thiols L-cysteine or L-cysteine methyl ester (FIG. 3) affected the liver levels of glutathione much less.

In this example, fasted mice were injected intraperitoneally with acetaminophen (2.5 mmol/kg), and one-half hour later (indicated by arrow in FIG. 3), they were given GSH monomethyl ester, GSH, L-cysteine, L-cysteine methyl ester (10 mmol/kg) or an equivalent volume of 0.15M NaCl (control). Tissue GSH levels were determined at the indicated intervals on groups (3) of mice; values are means ±S.D.

EXAMPLE 4

When mice were given a lethal dose of acetaminophen (5 mmole per kilogram) followed 1 hour later by glutathione monomethyl ester (10 mmole per kilogram), no fatalities were observed. In this study 15 mice were treated in this manner; all were found to be alive and apparently well 7 days later. In a group of 40 mice given the same dose of acetaminophen but no glutathione monomethyl ester, all of the mice died within 7 days.

EXAMPLE 5

Groups of 3 or 4 mice, each having a body weight of 18 to 22 g, were starved over a period of 12 hours and treated intraperitoneally with a dose of 7.5 mmol/kg of the test compound labeled by $^{35}S$ (GSH labeled by $^{35}S$ was used as the starting material). Two hours after the treatment, the test mice were dissected, and the liver and kidney were taken out. These organs were homogenized in 5 fold volume of 5% sulfosalicylic acid and centrifuged over a period of 5 minutes to give 0.05 ml of a supernatant fluid. The supernatant fluid was admixed with 0.95 ml of water and 4 ml of monofluorine scintillation fluid, and the $^{35}S$ content was assayed by the use of an LKB scintillation counter. On the other hand, the supernatant fluid was treated with monobromobimane and subjected to HPLC to determine the amount of the test compound. The intracellular GSH synthesis was inhibited by administering intraperitoneally 2 mmol/kg of buthionine sulfoximine 14 hours and 4 hours before the dissection.

In the group administered with an equal volume (0.86 ml) of 0.15M saline solution (the control group), the GSH levels in the liver and in the kidney were respectively 0.456 $\mu$mol/g and 0.200 $\mu$mol/g. In the group administered with GSH (the comparative group), the GSH levels in the liver and in the kidney were respectively 0.582 $\mu$mol/g and 0.560 $\mu$mol/g. In the group treated with the GSH monoalkyl ester (i.e. GSH monoisopropyl ester, monoisobutyl ester or mono-n-hexyl ester) (the medicated group), the GSH levels in the liver and in the kidney were respectively found to be more than 1.0 $\mu$mol/g and more than 2.0 $\mu$mol/g.

EXAMPLE 6

The test compound was dissolved in sterile water to give a test solution. Groups of 3 mice, each having a body weight of 20 to 25 g, were starved over a period of 24 hours and treated intraperitoneally with a dose of 10 mmol/kg of the test compound. Mice were dissected by every two hours, and the liver and kidney were taken out. GSH analysis was performed on each of the organs.

In the group treated with the GSH monoalkyl ester (i.e. GSH monoisopropyl ester, monoisobutyl ester or mono-n-hexyl ester) (the medicated group), the substantial elevation of GSH level in the liver was observed 2 to 3 hours after the administration, and the level lowered gradually thereafter. Likewise, the GSH level in the kidney showed the substantial elevation within the same period of time after the administration but then lowered.

Mice of the control group were treated with an equal volume of 0.15M saline solution, and no elevation of the GSH level was observed in the liver and in the kidney. Mice of the comparative group were treated with an equal volume of GSH. No elevation of the GSH level was observed in the liver, but slight elevation was observed in the kidney.

EXAMPLE 7

Groups of three starved mice were intraperitoneally treated with 2.5 mmol/kg (less than the lethal dose) of acetaminophen, and half an hour later 10 mmol/kg of the test compound was intraperitoneally administered to the mice. Marked fall of the GSH level in the liver was observed in the control group treated with an equal volume of 0.15M saline solution. On the other hand, such fall of the GSH level in the liver was not observed in the medicated group which received the GSH monoalkyl ester (i.e. GSH monoisopropyl ester, monoisobutyl ester or mono-n-hexyl ester) subsequently to the acetaminophen treatment, and rather marked elevation of the GSH level in the liver was observed. When other thiols such as L-cysteine and L-cysteine methyl ester were administered under the same conditions, the GSH level in the liver was markedly low.

EXAMPLE 8

Starved mice were intraperitoneally treated with 5 mmol/kg (lethal dose) of acetaminophen and, one hour later, with 10 mmol/kg of the test compound. All of 15 mice received the GSH monoalkyl ester (i.e. GSH monoisopropyl ester, monoisobutyl ester or mono-n-hexyl ester) (the medicated group) survived and were recovered clearly after 7 days. All of forty mice not receiving the GSH monoalkyl ester (the control group) were dead within seven days.

EXAMPLE 9

Male ICR mice, each having a body weight of 30 to 40 g, were starved over a period of 15 hours and intraperitoneally treated with 2.5 mmol/kg of acetaminophen. The acetaminophen was used as a solution in Cremophore buffer (i.e. physiological saline solution containing 10% Cremophore and 1.5% ethanol). Half an hour later a designed amount of the test compound was intraperitoneally administered to the mice. The test compound was used as a solution in physiological saline adjusted to pH 6.5. Eight hours after the administration of acetaminophen the mice were anesthetized with ether and allowed to bleed from the inferior vena cava. Then, the glutamic-pyruvic acid transaminase (GPT) activity in serum was assayed. The results are shown in Table 1 as a percentage to that of the control group to which only acetaminophen was administered.

The findings disclosed herein indicate that the administered glutathione ester is transported into the cells of the liver and kidney where it is hydrolyzed to glutathione. The studies in which mice were pretreated with buthionine sulfoximine provide strong evidence for transport of the glutathione esters; under these conditions, the synthesis of glutathione from its constituent amino acids is markedly inhibited.

It is also seen that intact glutathione is delivered into the cell, since glutathione synthesis is markedly inhibited by buthionine sulfoximine. Thus, the present method permits increasing the intracellular glutathione level in instances where a deficiency of the necessary synthetases for glutathione exists.

It is to be understood that the invention is not limited to the particular details described, for obvious modifications will occur to a person skilled in the art.

For example, the concept of the present invention could be used to form alkyl esters of other thiols which do not readily cross cellular membranes so as to transport them into cells. In addition, the esters of the present invention could be employed as safeners for plant crops by being administered thereto or to seeds prior to planting through absorbable liquid applications to protect the plants against the effects of herbicides being applied to combat weeds which are or might grow among the plant crops.

Variations of the invention will be apparent to the skilled artisan.

TABLE 1

| Compound | Dosage (mmol/kg) | | | | |
| --- | --- | --- | --- | --- | --- |
| | 0.01 | 0.03 | 0.1 | 0.3 | 1 |
| GSH | | | 105.3 ± 20.1 | 68.5 ± 16.3 | 4.2 ± 0.5 |
| GSH isopropyl ester | 75.2 ± 15.0 | 51.2 ± 15.6 | 19.8 ± 7.9 | 8.8 ± 3.5 | 3.8 ± 0.5 |
| GSH isobutyl ester | 84.1 ± 13.0 | | 44.8 ± 14.8 | | 3.6 ± 0.4 |
| GSH n-hexyl ester | 100.6 ± 31.3 | 82.3 ± 33.5 | 60.6 ± 15.8 | 13.2 ± 0.3 | 3.0 ± 0.3 |

Note:
Figure is a percentage of blood GPT activity to that of Control Group (± Standard Deviation (n = 4–16)).

What is claimed is:

1. A method for increasing cellular levels in plants of glutathione, comprising: administering a methyl and/or ethyl monoester of glutathione in substantially pure form in an amount to increase intracellular levels of glutathione, whereby said ester is transported into said cells and hydrolyzed intracellularly to glutathione, said ester being of the glycine carboxylic acid group of glutathione.

2. The method of claim 1 wherein said ester is the methyl ester.

3. The method of claim 1 wherein said ester is the ethyl ester.

4. A method for increasing radiation resistance of a plant comprising: administering a substantially pure monomethyl or monoethyl ester of glutathione, with the proviso that only the glycine carboxyl group of glutathione is esterified, in a dosage sufficient to increase the radiation resistance of said plant.

5. A method for safening plants by increasing their resistance to toxic effects of herbicides comprising treating crop plants or seeds thereof prior to planting with a methyl and/or ethyl monoester of glutathione, said ester being of the glycine carboxylic acid group of glutathione, to protect said crop plants against the toxic effects of a herbicide.

6. A method for increasing the resistance of a plant to the effects of reactive oxygen intermediates comprising: administering a substantially pure monomethyl or monoethyl ester of glutathione, with the proviso that only the glycine carboxyl group of glutathione is esterified, in a dosage sufficient to increase the resistance of said animal or plant to the effects of reactive oxygen intermediates.

7. A method for purifying monoethyl or monomethyl ester of glutathione admixed with corresponding diester, comprising dissolving the admixture in aqueous medium, adjusting the pH to about 8.0 to 9.2 and extracting the diester using an organic solvent immiscible with the aqueous medium.

8. A method for increasing cellular levels in plants of glutathione, comprising: administering an alkyl ($C_3$ to $C_{10}$) monoester of glutathione in substantially pure form in an amount to increase intracellular levels of glutathione, whereby said ester is transported into said cells and hydrolyzed intracellularly to glutathione, said ester being of the glycine carboxylic acid group of glutathione.

9. The method of claim 8 wherein said ester is a propyl ester.

10. The method of claim 8 wherein said ester is a butyl ester.

11. A method for increasing radiation resistance of a plant comprising: administering a substantially pure alkyl ($C_3$ to $C_{10}$) monoester of glutathione with the proviso that only the glycine carboxyl group of glutathione is esterified, in a dosage sufficient to increase the radiation resistance of said plant.

12. A method for safening plants by increasing their resistance to toxic effects of herbicides comprising treating crop plants or seeds thereof prior to planting with an alkyl ($C_3$ to $C_{10}$) monoester of glutathione, said ester being of the glycine carboxylic acid group of glutathione, to protect said crop plants against the toxic effects of a herbicide.

13. A method for increasing the resistance of a plant to the effects of reactive oxygen intermediates comprising: administering a substantially pure ($C_3$ to $C_{10}$) monoester of glutathione, with the proviso that only the glycine carboxyl group of glutathione is esterified, in a dosage sufficient to increase the resistance of said plant to the effects of reactive oxygen intermediates.

14. A method for purifying alkyl ($C_3$ to $C_{10}$) monoester of glutathione admixed with corresponding diester, comprising dissolving the admixture in aqueous medium, adjusting the pH to about 8.0 to 9.2 and extracting the diester using an organic solvent immiscible with the aqueous medium.

* * * * *